(12) United States Patent
Okoniewski

(10) Patent No.: US 8,596,515 B2
(45) Date of Patent: Dec. 3, 2013

(54) STAPLE POSITION SENSOR SYSTEM

(75) Inventor: Gregory Okoniewski, New Haven, CT (US)

(73) Assignee: Covidien LP, Mansfield, MA (US)

( * ) Notice: Subject to any disclaimer, the term of this patent is extended or adjusted under 35 U.S.C. 154(b) by 203 days.

(21) Appl. No.: 13/086,547

(22) Filed: Apr. 14, 2011

(65) Prior Publication Data

US 2011/0309128 A1 Dec. 22, 2011

Related U.S. Application Data

(60) Provisional application No. 61/356,195, filed on Jun. 18, 2010.

(51) Int. Cl.
*A61B 17/068* (2006.01)

(52) U.S. Cl.
USPC .................. 227/176.1; 227/19; 227/180.1

(58) Field of Classification Search
USPC .............. 227/19, 176.1, 177.1, 178.1, 180.1; 606/142, 216
See application file for complete search history.

(56) References Cited

U.S. PATENT DOCUMENTS

| | | | |
|---|---|---|---|
| 5,383,880 A | 1/1995 | Hooven | |
| 5,395,033 A * | 3/1995 | Byrne et al. | 227/175.1 |
| 5,503,320 A | 4/1996 | Webster et al. | |
| 5,518,163 A | 5/1996 | Hooven | |
| 5,518,164 A | 5/1996 | Hooven | |
| 5,535,934 A | 7/1996 | Boiarski et al. | |
| 5,535,937 A | 7/1996 | Boiarski et al. | |
| 5,562,239 A | 10/1996 | Boiarski et al. | |
| 6,671,185 B2 * | 12/2003 | Duval | 361/807 |
| 2004/0126201 A1 * | 7/2004 | Kobylinski et al. | 411/13 |
| 2005/0070958 A1 | 3/2005 | Swayze et al. | |
| 2005/0131390 A1 * | 6/2005 | Heinrich et al. | 606/1 |
| 2006/0097025 A1 | 5/2006 | Milliman et al. | |
| 2006/0273135 A1 | 12/2006 | Beetel | |
| 2008/0255413 A1 | 10/2008 | Zemlok | |
| 2008/0312687 A1 | 12/2008 | Blier | |

OTHER PUBLICATIONS

European Search Report for corresponding EP11250596 date of mailing is Nov. 16, 2011 (3 pgs).

* cited by examiner

*Primary Examiner* — Alexandra Elve
*Assistant Examiner* — Nathaniel Chukwurah

(57) ABSTRACT

A surgical stapling instrument includes a handle assembly, an elongate shaft extending distally from the handle assembly, and a tool assembly coupled to a distal end of the elongate shaft. The tool assembly includes a cartridge assembly including a plurality of surgical staples each including a code embedded portion and a first sensor for detecting the position of the surgical staples prior to and during a formation of the staples. The tool assembly further includes an anvil assembly including a second sensor that detects the position of the surgical staples after the formation of the surgical staples.

14 Claims, 11 Drawing Sheets

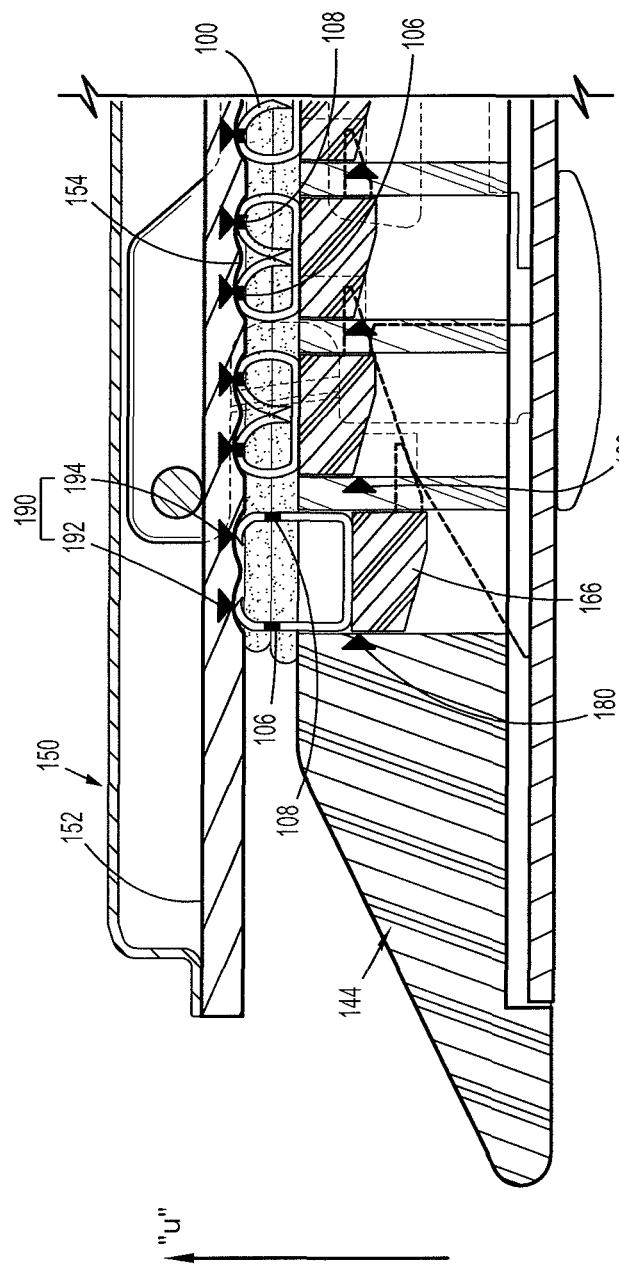
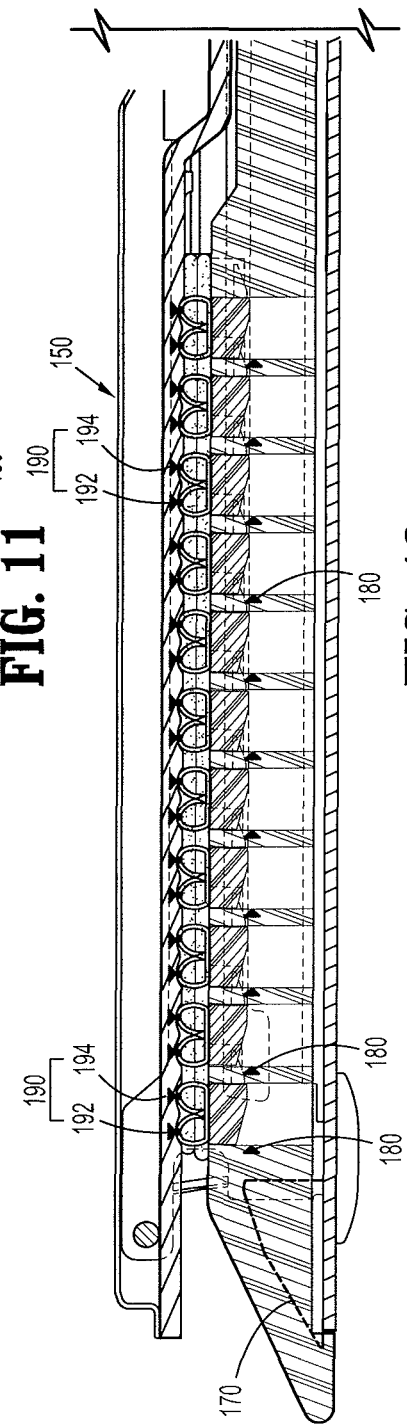
FIG. 11
FIG. 12

STAPLE POSITION SENSOR SYSTEM

CROSS REFERENCE TO RELATED APPLICATION

The present application claims the benefit of and priority to U.S. Provisional Application Ser. No. 61/356,195 filed on Jun. 18, 2010, the entire contents of which are incorporated herein by reference.

BACKGROUND

1. Technical Field

The present disclosure relates to a surgical stapling instrument and, more particularly, to a staple position sensor system.

2. Background of Related Art

Surgical stapling instruments used for sequentially applying linear rows of surgical staples through tissue are well known in the art. Surgical staplers of this type may be used during an open surgical procedure where an incision is made to provide access to the surgical site or during an endoscopic or laparoscopic surgical procedure where stapling is accomplished through a generally cylindrical access tube. Endoscopic and laparoscopic surgical instruments are often preferred over traditional open surgical devices since a smaller incision tends to reduce the post-operation recovery time and complications.

Known surgical stapling instruments include an end effector that simultaneously makes a longitudinal incision in tissue and applies lines of staples on opposing sides of the incision. The end effector includes a pair of cooperating jaw members that, if the instrument is intended for endoscopic or laparoscopic applications, is capable of passing through a cannula passageway. One of the jaw members includes a staple cartridge assembly having laterally spaced rows of staples. The other jaw member includes an anvil assembly defining staple forming concavities aligned with the rows of staples in the cartridge assembly. The surgical stapler further includes an actuation sled, which sequentially engages a plurality of pushers supporting staples in the staple cartridge assembly. Movement of the plurality of pushers ejects the staples from the staple cartridge assembly and presses the ejected staples against surfaces of concavity on the anvil assembly to form and close the staples in tissue. Staples in an unformed condition include a backspan and a pair of legs projecting from the backspan. When properly formed, the staples assume a substantially "B-shaped" configuration. Improperly formed staples can cause adverse consequences, such as, for example, inadequate hemostasis.

SUMMARY

In accordance with an embodiment of the present disclosure, there is provided a surgical stapling instrument including a surgical staple containing a code embedded portion and a tool assembly including a cartridge assembly and an anvil assembly selectively positionable relative to the cartridge assembly about a pivot. The code embedded portion of the staple may be a code readable by magnetic, electronic or optical sensors. The cartridge assembly includes a first sensor for detecting a position of the code embedded portion of the surgical staple. The anvil assembly includes a second sensor for detecting the position of the code embedded portion of the surgical staple when the surgical staple is in contact with the anvil assembly.

In an embodiment, the surgical staple may include a backspan and a pair of legs extending from the backspan. At least one of the pair of legs includes the code embedded portion. In some embodiments, the cartridge assembly may define a retention channel for accommodating therein the surgical staple. The first sensor is disposed adjacent the retention channel. In some embodiments, the code embedded portion aligns with the first sensor when the surgical staple is properly loaded in the retention channel prior to the formation of the staple. Alternatively, the first sensor may be exposed in the retention channel. In some cases, the first sensor may be in a direct contact with the code embedded portion when the surgical staple is properly loaded in the retention channel prior to the formation of the surgical staple.

In an embodiment, the anvil assembly may define a concavity. The second sensor is disposed adjacent the concavity. The code embedded portion of the surgical staple aligns with the second sensor after a proper formation of the surgical staple. Alternatively, the second sensor may be exposed in the concavity. In some cases, the second sensor may be in a direct contact with the code embedded portion after a proper formation of the surgical staple. In an embodiment, the concavity may include a pair of recesses. Each recess is configured to deform respective leg of the surgical staple. In an embodiment, the second sensor is disposed adjacent one of the pair of recesses such that the code embedded portion aligns with the second sensor after a proper formation of the surgical staple. In some embodiments, the backspan of the surgical staple may define a groove.

In an embodiment, the first sensor may be configured to detect a position of the code embedded portion of the surgical staple in an unformed state, and the second sensor may be configured to detect the position of the code embedded portion of the surgical staple in a formed state.

In accordance with another embodiment of the present disclosure, there is provided a surgical stapling instrument including a handle assembly, an elongate shaft extending longitudinally from the handle assembly, a tool assembly including a cartridge assembly and an anvil assembly selectively positionable relative to the cartridge assembly about a pivot, and a surgical staple including a code embedded portion. The cartridge assembly defines a retention channel and the anvil assembly defines a concavity.

In an embodiment, the cartridge assembly includes a first sensor for detecting a position of the code embedded portion of the surgical staple. In another embodiment, the anvil assembly includes a second sensor for detecting the position of the code embedded portion of the surgical staple when the surgical staple is in contact with the anvil assembly.

BRIEF DESCRIPTION OF THE DRAWINGS

The above and other objects and features of the present disclosure will become apparent from the following description of embodiments given in conjunction with the accompanying drawings, in which:

FIG. 11 is a partial longitudinal cross-sectional view of the tool assembly of FIG. 9 illustrating formation of the surgical staples;

FIG. 12 is a partial longitudinal cross-sectional view of the tool assembly of FIG. 9 after a formation of the surgical staples;

DETAILED DESCRIPTION

Figure 1:
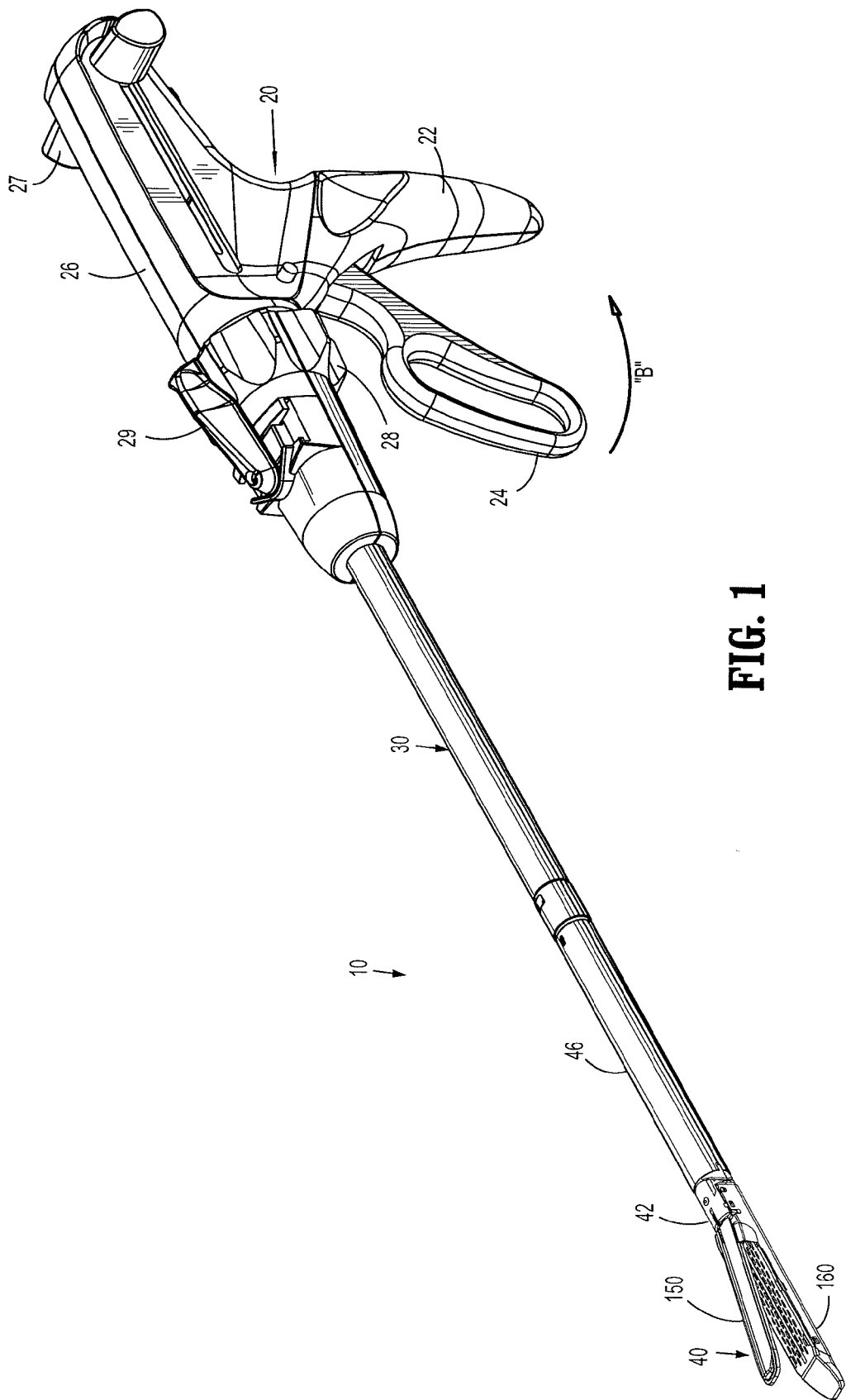
FIG. 1 is a perspective view of a surgical stapling apparatus.

Various embodiments of the presently disclosed surgical stapling apparatus will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator.

A surgical stapling apparatus is illustrated in FIG. 1 and is designated by the reference numeral 10. Surgical stapling apparatus 10 includes a handle assembly 20, an elongate body 30 extending distally from handle assembly 20 and a disposable loading unit 40 releasably secured to a distal end of elongate body 30. Disposable loading unit 40 includes a tool assembly 42 having a cartridge assembly 160 and an anvil assembly 150 movably secured in relation to cartridge assembly 160. Disposable loading unit 40 is configured to sequentially apply linear rows of staples.

Handle assembly 20 includes a stationary handle member 22, a movable handle member 24, and a barrel portion 26. A rotatable member 28 is mounted on barrel portion 26 to facilitate rotation of elongated body 30 with respect to handle assembly 20. An articulation lever 29 is provided on a distal end portion of barrel portion 26 adjacent rotatable knob 28 to facilitate articulation of tool assembly 42. An actuation shaft (not shown) is supported within barrel portion 26. The actuation shaft is operatively coupled to movable handle member 24 such that pivotal movement of handle member 24 in the direction of an arrow "B" in FIG. 1 advances the actuation shaft axially which in turn causes firing of the surgical staples. A retraction knob 27 is attached to the actuation shaft. Retraction knob 27 is movably positioned along barrel portion 26 to return the actuation shaft to a retracted position.

Figure 2:
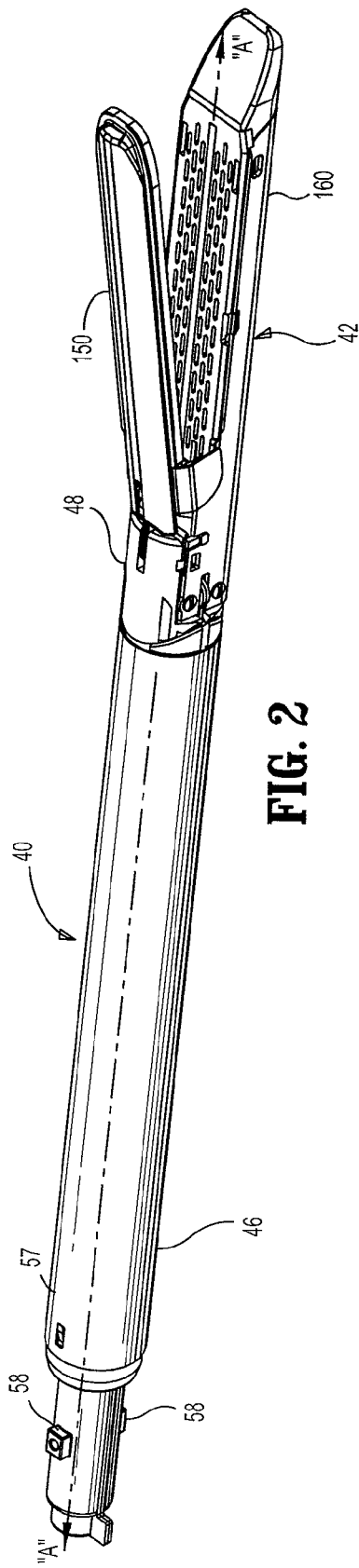
FIG. 2 is a perspective view of a disposable loading unit of the surgical stapling apparatus of FIG. 1.
Figure 3:
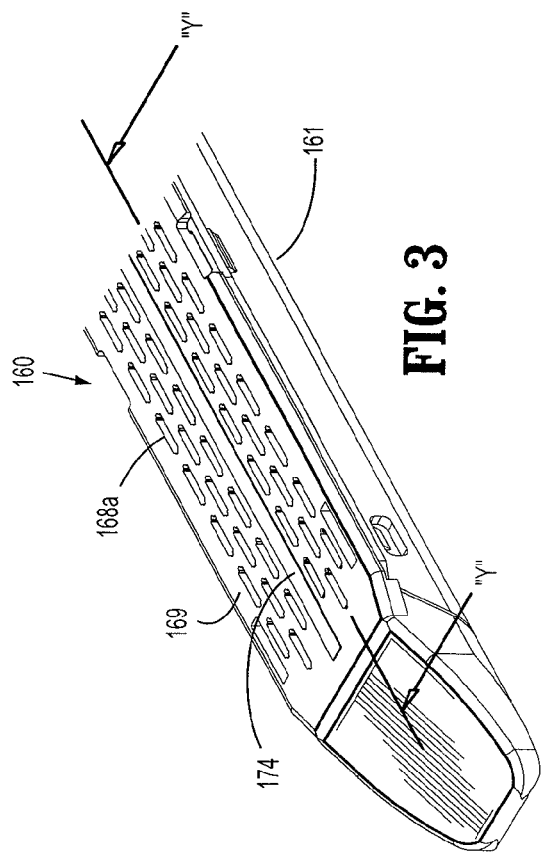
FIG. 3 is a partially enlarged perspective view of a distal end of a staple cartridge of the surgical stapling apparatus of FIG. 1.

With reference now to FIG. 2, disposable loading unit 40 includes tool assembly 42 and a proximal housing portion 46 adapted to releasably engage disposable loading unit 40 to elongate body 30. A mounting assembly 48 is pivotally secured to a distal end portion of housing portion 46 such that pivotal movement of mounting assembly 48 about an axis perpendicular to the longitudinal axis "A-A" of housing portion 46 effects articulation of tool assembly 42. With disposable loading unit 40 attached to stapling instrument 10, tool assembly 42 can be positioned about tissue. To clamp tissue between anvil assembly 150 and cartridge assembly 160, stationary handle member 22 is moved in the direction indicated by arrow "B" in FIG. 1. One complete stroke of movable handle member 24 advances the actuation shaft just enough to clamp tissue during the first stroke but not to fire staples (i.e., approximate anvil assembly 150 and cartridge assembly 160). In order to fire staples, movable handle member 24 is actuated again, i.e., moved through another stroke.

Figure 6:
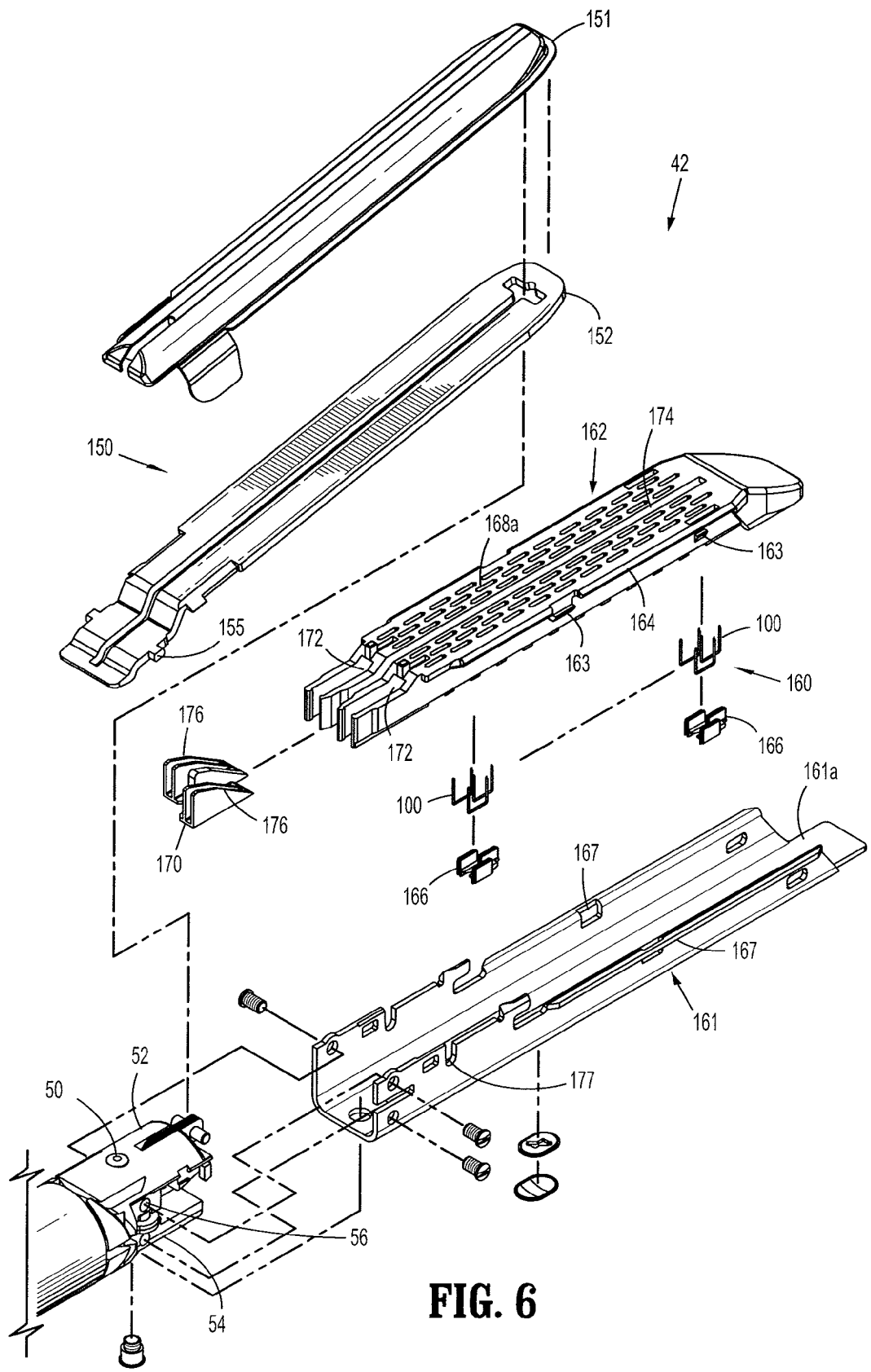
FIG. 6 is a perspective view of a tool assembly of the surgical stapling apparatus of FIG. 1 with parts separated.

Tool assembly 42 includes anvil assembly 150 and cartridge assembly 160. As best seen in FIG. 6, anvil assembly 150 includes an anvil portion 152 defining a plurality of surgical staple deforming concavities 154 and a cover plate 151 secured to a top surface of anvil portion 152. With reference to FIGS. 3-6, staple cartridge assembly 160 includes a staple cartridge 162 defining a plurality of retention channels 168 and a cartridge base plate 161 releasably coupled to a bottom portion of staple cartridge 162. Cartridge base plate 161 defines an elongated support channel 161a which is dimensioned and configured to receive staple cartridge 162. Corresponding tabs 163 and slots 167 formed along staple cartridge 162 and cartridge base plate 161, respectively, function to retain staple cartridge 162 within support channel 161a. A pair of support struts 164 formed on staple cartridge 162 is positioned to rest on side walls of cartridge base plate 161 to further stabilize staple cartridge 162 within support channel 161a. A pair of pivot members 155 formed on anvil portion 152 are positioned within slots 177 formed in cartridge base plate 161 to guide anvil portion 152 between the open and clamped positions.

Figure 4:
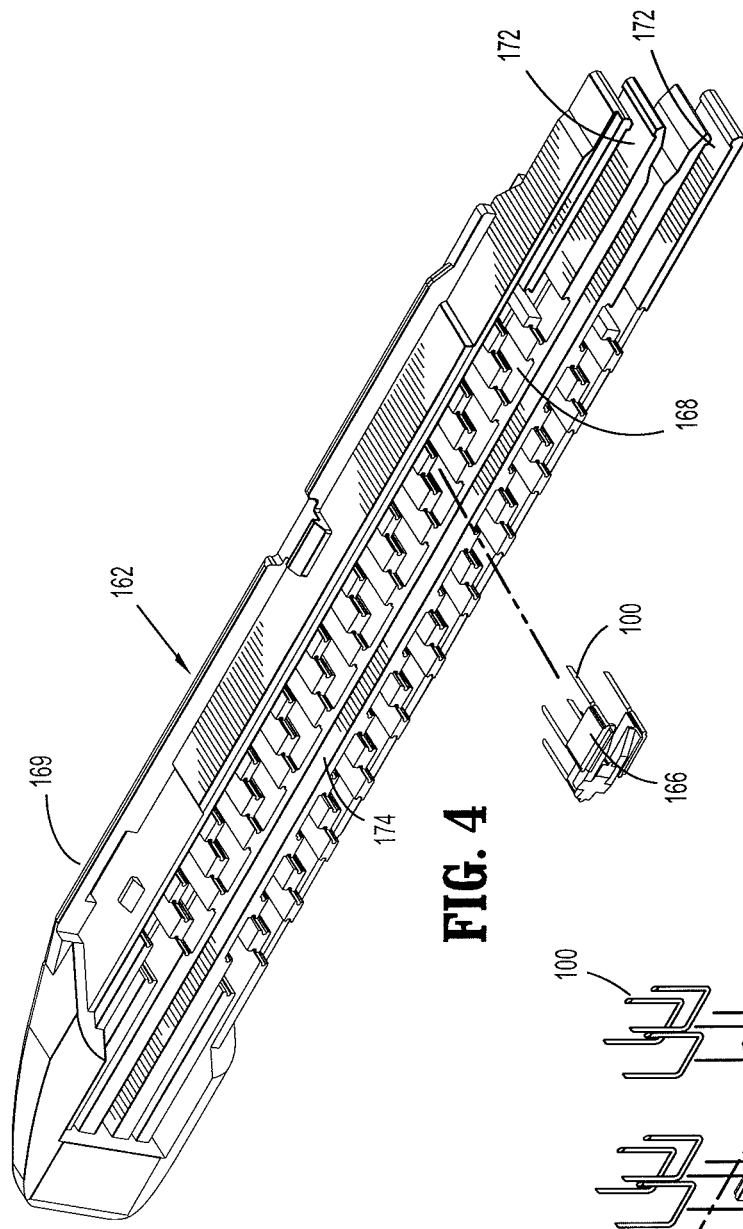
FIG. 4 is a bottom perspective view of the staple cartridge of FIG. 1.
Figure 5:
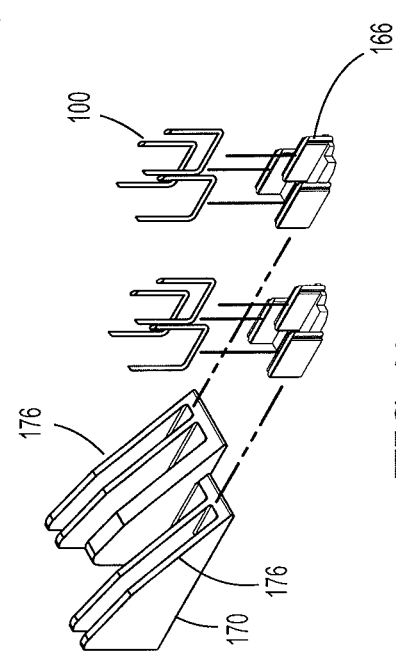
FIG. 5 is an enlarged perspective view of an actuation sled, pushers and staples.

Retention channels 168, as best shown in FIG. 4, extend from a bottom portion of staple cartridge 162 adjacent base plate 161 to a tissue contacting surface 169. Tissue contacting surface 169 defines a plurality of slots 168a in communication with retention channels 168. Retention channels 168 and slots 168a align with the plurality of surgical staple deforming concavities 154 of anvil assembly 150. The plurality of retention channels 168 accommodates therein a plurality of pushers 166 and surgical staples 100 having code embedded portions, as will be described in detail below.

Each surgical staple 100 is supported on respective pusher 166. Staple cartridge 162 further defines spaced apart longitudinal slots 172 adapted to receive therein an axially translating actuation sled 170, as best shown in FIG. 4. As actuation sled 170 translates distally through longitudinal slots 172 of staple cartridge 162 cam wedges 176 sequentially engage pushers 166. Cam wedges 176 cause pushers 166 to translate toward tissue contacting surface 169 within retention channels 168 and thereby ejecting staples 100 from slots 168a towards the staple deforming concavities 154 of anvil assembly 150. Optionally, a longitudinally extending central slot 174 may be further provided on staple cartridge 162 to facilitate passage of a knife blade (not shown) which allows for a simultaneous separation of tissue while applying lines of staples 100 on opposing sides of the cut line.

As best seen in FIG. 2, proximal housing portion 46 of disposable loading unit 40 is formed of an upper housing half and a lower housing half contained within an outer casing 57. The proximal end of proximal housing portion 46 includes engagement nubs 58 for releasable engagement with elongate body 30 through, e.g., a bayonet type coupling with a distal end portion of elongate body 30. An example of a suitable stapling instrument is disclosed in U.S. Pat. No. 6,953,139, the entire contents of which are hereby incorporated by reference.

Figure 7:
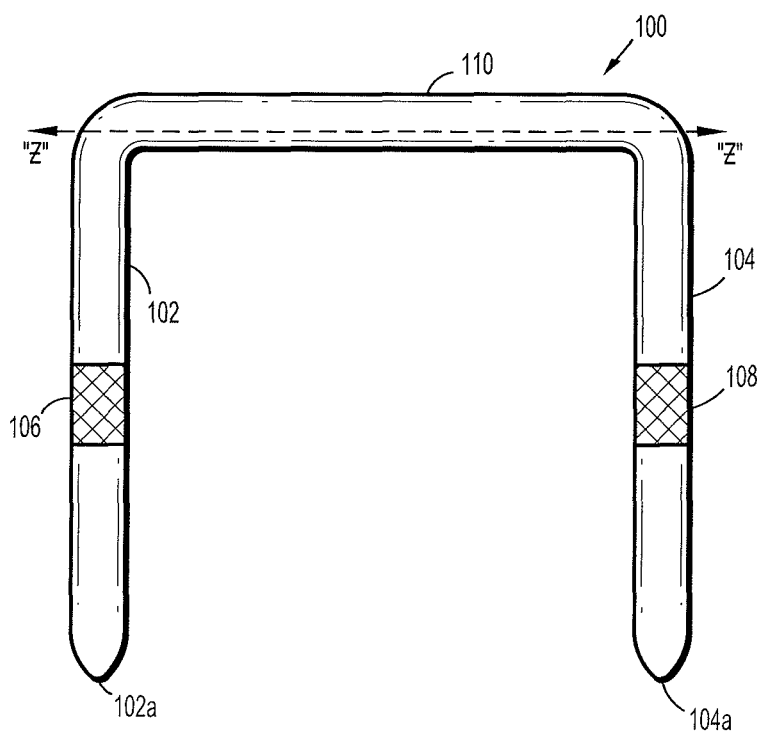
FIG. 7 is a cross-sectional view of a surgical staple in accordance with an embodiment of the present disclosure.

Referring now to FIG. 7, an embodiment of the present disclosure is shown generally as a surgical staple 100. Staple 100 includes a pair of legs 102, 104 and a backspan 110. Each leg 102, 104 includes a respective code embedded portion 106, 108 and a respective penetrating distal tip 102a, 104a configured and dimensioned to penetrate tissue. In an unformed position, staple 100 has a substantially flat profile with legs 102, 104 in the same plane as backspan 110. In particular, legs 102, 104 are substantially straight and perpendicular to a longitudinal axis "Z-Z" of backspan 110. However, legs 102, 104 need not be parallel as legs 102, 104 can also be positioned at other angles with respect to backspan 110, i.e., non-perpendicular to backspan 110.

Figure 8:
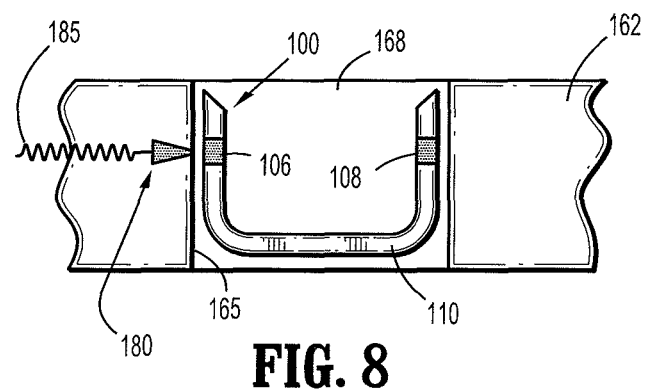
FIG. 8 is a partial longitudinal cross-sectional view of a cartridge assembly having the surgical staple of FIG. 6 loaded therein.
Figure 9:
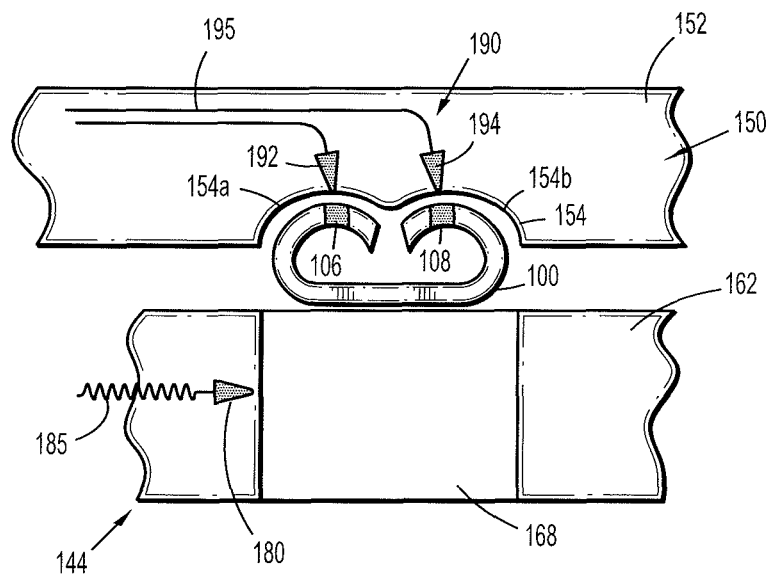
FIG. 9 is a partial longitudinal cross-sectional view of a tool assembly after a formation of the surgical staple of FIG. 6.
Figure 10:
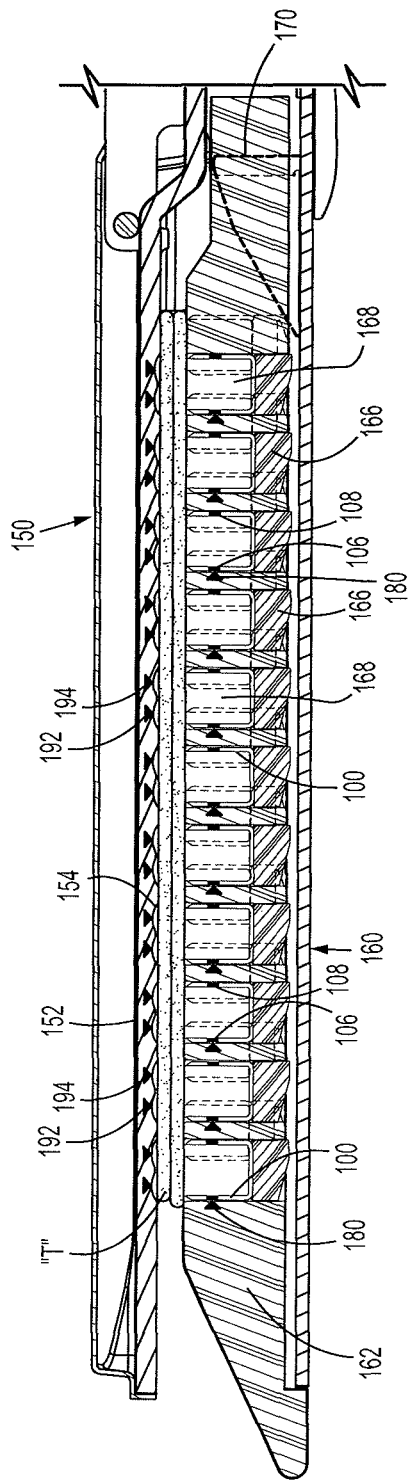
FIG. 10 is a partial longitudinal cross-sectional view of a tool assembly in accordance with an embodiment of the present disclosure in a clamped position.

With reference to FIGS. 8-10, staple cartridge 162 includes a plurality of sensors 180. As best shown in FIG. 8, each sensor 180 is embedded in a side wall 165 defining a retention channel 168 in which staple 100 is loaded prior to being ejected. Sensor 180 is placed in side wall 165 such that when staple 100 is properly loaded in retention channel 168 and supported on a respective staple pusher 166, code embedded portions 106, 108 of staple 100 are aligned with sensor 180. Sensor 180 may employ, for example, mechanical, optical, magnetic or electrical means, to determine whether code embedded portions 106, 108 are aligned with sensor 180. In particular, sensor 180 may be exposed in retention channel 168. In some cases, sensor 180 exposed in retention channel 168 may be in a direct contact with one of code embedded portions 106, 108 when surgical staple 100 is properly loaded in respective retention channel 168. The data collected by sensors 180, i.e., whether code embedded portions 106, 108 are aligned with respective sensor 180, may be sent to a user in a relatively remote location through an electrical wire 185 or wireless means (not shown). Such data may be processed by a processing unit, which may be provided on handle assembly 20 or an external terminal (not shown). Sensor 180 in conjunction with staple 100 allows a user to monitor the position/state of staple 100 prior to and during a formation of surgical staples 100.

The code embedded portion of the staples 106, 108 may be a code readable by magnetic, electronic or optical sensors 180. Thus in the instance of a magnetic sensor 180, the sensor 180 may be a hall effect sensor and the code embedded sensor portion 106, 108 may coated with be a magnetic ink. Similarly, an electronic sensor 180 may, for example, measure the resistance of the code embedded portion of the staples 106, 108 which may be plated with a low resistance biocompatible material such as silver or coated with a high resistance material such as a polymer. Optical sensors 180 may be implemented with code embedded portion of the staples 106, 108 painted or otherwise processed to modify the color, reflectance or other optical qualities.

Placement of sensor 180, however, may be tailored to meet the specific needs of a surgical procedure being performed. For example, sensor 180 may be placed in a position offset from code embedded portions 106, 108 of a properly loaded staple 100, such that when staple 100 is improperly loaded in channel 168 code embedded portions 106, 108 are aligned with sensor 180 placed in the offset position. Thus, sensor 180 detects the improperly loaded staple 100. In addition, sensor 180 placed in the offset position may detect firing or misfiring of a properly loaded staples 100. In the case of proper firing of staple 100, sensor 180 in the offset position may detect passage of code embedded portions 106, 108 of staple 100. In the case of misfiring of staple 100, sensor 1800 may detect code embedded portions 106, 108 of misfired staple 100 positioned in the offset position, i.e., code embedded portions 106, 108 do not pass by sensor 180 in the offset position, but rather aligns with sensor 180 in the offset position. Furthermore, it is envisioned that code embedded portions 106, 108 may be placed in backspan 110 to detect proper loading and/or misfiring of staples 100. Under such arrangement, sensor 180 will be placed in a bottom portion of cartridge 162 or in cartridge base plate 161.

With continued reference to FIGS. 9 and 10, anvil assembly 150 includes an anvil sensor system 190, anvil portion 152 defining a plurality of concavities 154 and cover plate 151 secured to a top surface of anvil portion 152. As best seen in FIG. 9, each concavity 154 includes concave portions 154a, 154b for deforming respective legs 102, 104. A pair of sensors 192, 194 is embedded adjacent respective concave portion 154a, 154b of concavity 154 such that when staple 100 is properly formed against concave portions 154a, 154b of concavity 154, and thereby rendering a "B-shaped" staple 100, code embedded portions 106, 108 are aligned with sensors 192, 194, respectively. Similar to sensor 180, sensors 192, 194 may employ, for example, mechanical, optical, magnetic or electrical, means, to determine whether code embedded portions 106, 108 of staple 100 are aligned with respective sensors 192, 194. It is contemplated that in some cases, sensors 192, 194 embedded in anvil portion 152 may be partially exposed to code embedded portions 106, 108. In particular, code embedded portions 106, 108 of a staple 100 may be in a direct contact with sensors 192, 194, respectively, after a proper formation of staple 100. Further, the code embedded portion of the staples 106, 108 may have the code modified by the deformation of staple formation or mechanical scraping during deformation. Thus a magnetic ink may be removed or the magnetic field diminished, a resistance may be altered or an optical characteristic altered of the code embedded portion of the staples 106, 108 such that data from sensors 180 and sensors 192, 194 may be compared to further ensure correct formation.

Sensors 192, 194 transmit signals to a relatively remote location through an electrical wire 195 or wireless means (not shown) where the signal is processed by a processing unit. The data processed by the processing unit is displayed on handle assembly 20 or on an external terminal (not shown) for a user who will monitor whether staples 100 have been properly formed, i.e., whether code embedded portions 106, 108 are properly aligned with respective sensor 192, 194. Alternatively, the output data may be directly processed by an automated/processor driven system to control staple formation. In either case, anvil sensor system 190 in conjunction with staple 100 allows the user to monitor the position/state of staple 100 after the firing of surgical staples 100 and thereby determining whether a proper formation of staples 100 has taken place. By employing anvil sensor system 190 and cartridge sensor 180, the user can verify staple presence prior to instrument use and proper staple formation post-firing of surgical staples 100. In addition, the user can monitor whether all staples have been fired. Moreover, the user can control staple formation to prevent under or over forming of staples and/or to compensate varying tissue thickness or characteristics. It is further contemplated that sensors 192, 194 may be positioned offset from code embedded portions 106, 108 of a properly formed staple 100 such that code embedded portions 106, 108 of an improperly formed staple 100 aligns with sensors 192, 194 in the offset positions, as described with sensor 180.

In use, with tissue "T" clamped between anvil assembly 150 and cartridge assembly 160 as shown in FIG. 10, surgical stapling instrument 10 is used in accordance with methods known by those skilled in the art. At this time, staples 100 including code embedded portions 106, 108 are loaded in respective retention channel 168. Staple 100 properly supported on respective pusher 166 within retention channel 168 allows code embedded portions 106, 108 to be aligned with sensor 180 embedded in respective side wall 165 of retention channel 168. As noted above, sensor 180 which may employ, e.g., mechanical, optical, magnetic or electrical means, to determine whether code embedded portion 106, 108 are aligned with sensor 180, sends the data obtained by sensor 180 through electrical wire 185 or wireless means (not shown) to a processing unit that is at a relatively remote location. As described above, the data may be processed by a processing unit, which may be provided on handle assembly 20 or on an external terminal (not shown). As such, sensor 180 in conjunction with staple 100 allows the user to monitor the position/state of the plurality of surgical staples 100 prior to and during firing of the plurality of surgical staples 100.

Upon determining that staples 100 are properly loaded in respective retention channel 168, i.e., each code embedded portion 106, 108 of staple 100 is aligned with respective sensor 180, the user is now ready to fire staples 100 into tissue "T" for, e.g., closure of tissue prior to resection or for occlusion of organs. The user fires staples 100 by manipulating handle assembly 20 as described above. Manipulation of handle assembly 20 causes axial movement of the actuation shaft in the distal direction, which in turn drives actuation sled 170 distally. Cam wedges 176 sequentially come into a contact with a plurality of pushers 166, which in turn forces pushers 166 to advance towards anvil assembly 150 in the direction of an arrow "U," as shown in FIG. 11. Each staple 100 supported on respective pusher 166 is pushed towards anvil assembly 150 and is ejected from retention slot 168a through tissue "T." Penetrating distal tips 102a, 104a of staple 100 are pushed against concavity 154 and are buckled towards backspan 110, thereby forming a "B-shaped" staple 100. As shown in FIG. 11, a properly formed "B-shaped" staple 100 provides code embedded portions 106, 108 to align with respective sensors 192, 194 disposed adjacent respective concave portions 154a, 154b in anvil portion 152. As noted above, depending on the type of sensor 180 used, sensors 192, 194 may be positioned within anvil portion 152 adjacent concavity 154 such that a direct contact occurs between code embedded portions 106, 108 and respective sensors 192, 194 when staple 100 has been properly formed.

Then sensors 192, 194 transmit signals to the processing unit located at a relatively remote location, through electrical wire 195 or wireless means. The processing unit processes the signal and displays on handle assembly 20 or on an external display terminal whether proper formation of staples 100 has taken place. The user who monitors whether staples 100 have been properly formed, i.e., whether code embedded portions 106, 108 are properly aligned with respective sensor 192, 194, will determine the next course of action. As such, anvil sensor system 190 in conjunction with staple 100 allows the user to monitor the position/state of staple 100 after and during firing.

As shown in FIG. 11, the distal-most staple 100 which does not have a completely formed "B-shape" configuration lacks proper alignment between code embedded portions 106, 108 and respective sensors 192, 194. Such state will be displayed on handle assembly 20 or on the external display terminal.

Now turning to FIG. 12, stapling of tissue "T" is complete, as indicated by proper formation of "B-shaped" staples 100 and further evidenced by actuation sled 170 at the distal-most position of staple cartridge 162. Here, all staples 100 have been properly formed. As such, code embedded portions 106, 108 of each individual staple 100 are properly aligned with respective sensors 192, 194. At this time, sensor system 190 sends the collected data indicating proper formation of all staples 100 to a relatively remote location where the user can process the data. At this time, the user can perform other surgical procedures knowing that all surgical staples 100 have been properly formed. However, if any one of the plurality of surgical staple 100 is defectively or incompletely formed, the user may repeat the process to correct the problem prior to carrying out other surgical procedures.

Figure 13:
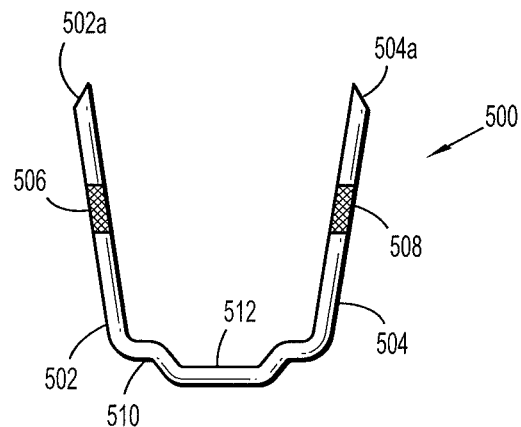
FIG. 13 is a cross-sectional view of a surgical staple in accordance with another embodiment of the present disclosure.
Figure 14:
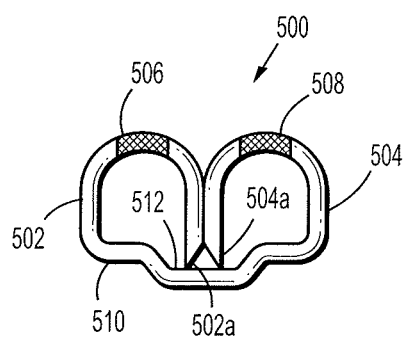
FIG. 14 is a cross-sectional view of the surgical staple of FIG. 12 after a formation of the surgical staple.

With reference to FIGS. 13 and 14, another embodiment of a surgical staple 500 having code embedded portions 506, 508 in accordance with the present disclosure is illustrated. Staple 500 includes a backspan 510 defining a groove 512 and a pair of legs 502, 504 with tissue penetrating tips 502a, 504a, respectively. The pair of legs 502, 204 extends from backspan 510 at an angle, i.e., non-perpendicular to backspan 510. The groove 512 provides additional length of travel for the pair of legs 502, 504 in a case of thin tissue. As such, even in the case of stapling a thin tissue, tissue penetrating tips 502a, 504a will not be driven into backspan 510 causing undesirable bending of surgical staple 500. Moreover, such design inhibits legs 502, 504 from being driven past backspan 510, which in turn may inhibit puncturing of neighboring tissue. The operation and use of staple 500 is substantially identical to staple 100 and will be omitted in the interest of brevity.

Figure 15:
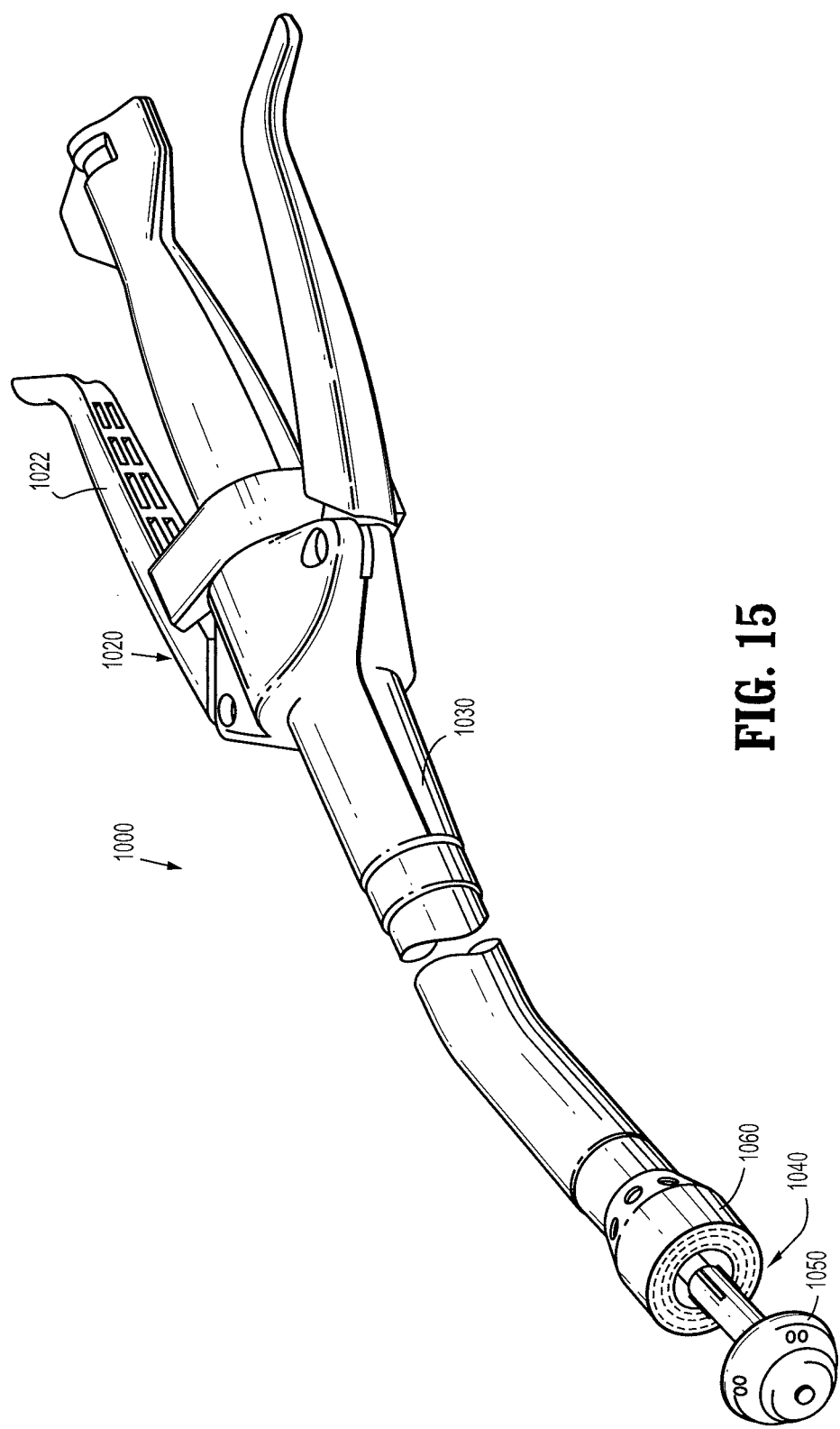
FIG. 15 is a perspective view of a circular stapling instrument.
Figure 16:
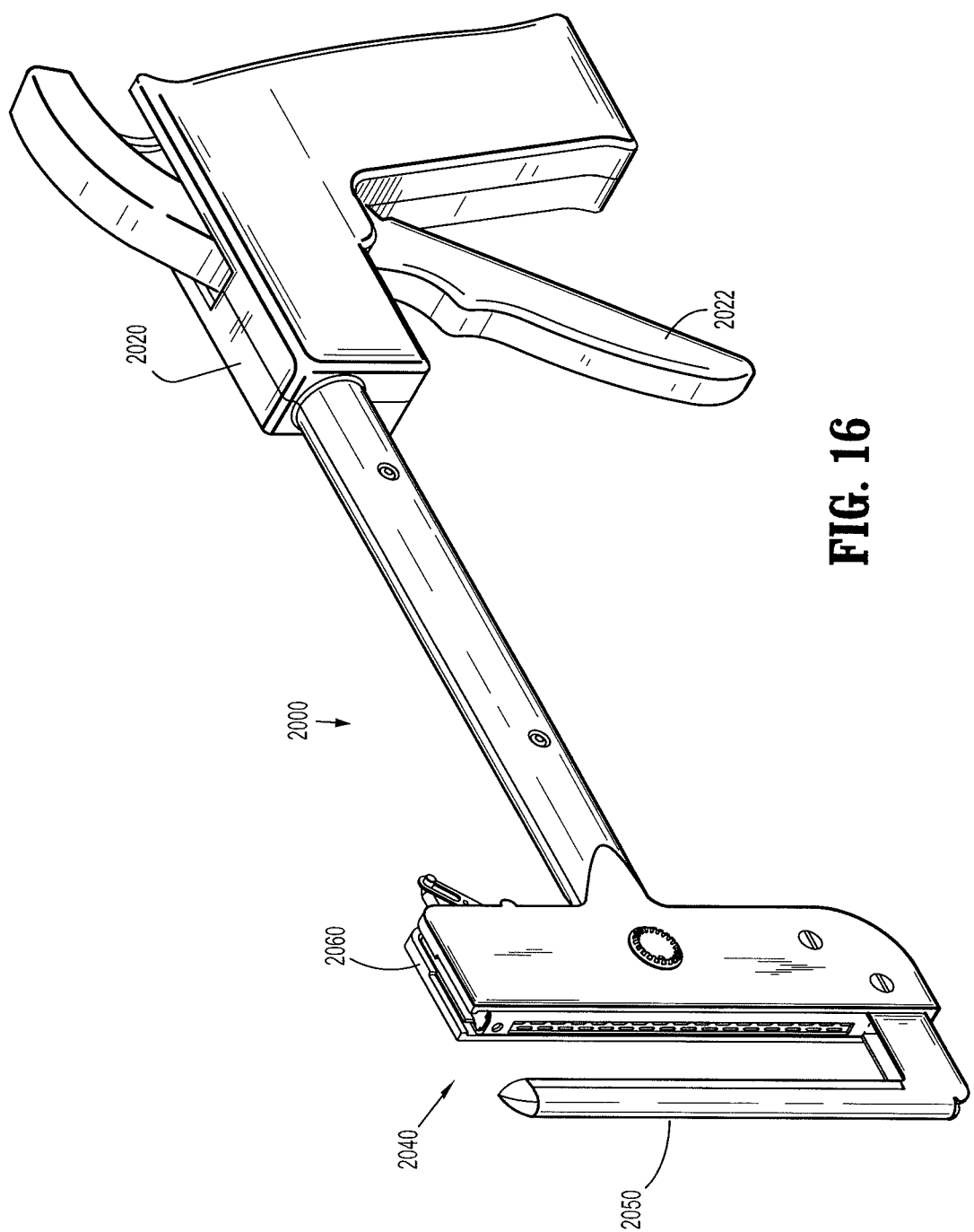
FIG. 16 is a perspective view of a transverse stapling instrument.

As shown in FIGS. 15 and 16, it is further contemplated that the disclosed staple position sensor system can be configured for use with, for example, a circular stapling apparatus 1000, as well as a transverse stapling apparatus 2000. Typically, each of these devices includes a housing 1020, 2020 having an actuator 1022, 2022, an actuation mechanism operatively coupled to actuator 1022, 2022 and a tool assembly 1040, 2040. Each actuator 1022, 2022 is movable to effect advancement of the actuation mechanism which effects formation of staples 100 against a plurality of concavities defined in each anvil assembly 1050, 2050. Tool assembly 1040, 2040 is operatively coupled to the actuation mechanism. Each tool assembly 1040, 2040 has a cartridge assembly 1060, 2060 and an anvil assembly 1050, 2050 movably mounted in relation to cartridge assembly 1060, 2060. Each tool assembly 1040, 2040 accommodates the staple position sensor system described above. In particular, a plurality of staples 100 having code embedded portions 106, 108 are disposed in cartridge assembles 1060, 2060. Cartridge assembles 1060, 2060 each include sensors that detect proper loading of staples 100 in retention channels in cartridge assemblies 1060, 2060. Each anvil assembly 1050, 2050 includes an anvil sensor system including a pair of sensors disposed adjacent concavity portions defined in respective anvil assemblies 1050, 2050. It should be noted that while the staple position sensor system of the present disclosure has been described in detail in above-embodiments with respect to endoscopic/laparoscopic instruments, the staple position sensor system is not limited to such stapling instruments. Staple position sensor system of the present disclosure can be utilized in instruments used in open surgical procedures, such as transverse stapling apparatus 2000 shown in FIG. 16.

It will be understood that various modifications may be made to the embodiments of the presently disclosed surgical clamp and clamp applier. Therefore, the above description should not be construed as limiting, but merely as exemplifications of embodiments. Those skilled in the art will envision other modifications within the scope and spirit of the present disclosure.

What is claimed is:

1. A surgical stapling instrument comprising:
a handle assembly;
an elongate shaft extending longitudinally from the handle assembly;
a tool assembly including a cartridge assembly and an anvil assembly selectively positionable relative to the cartridge assembly about a pivot, the cartridge assembly defining a retention channel, the anvil assembly defining a concavity; and
a surgical staple including a backspan and a pair of legs extending from the backspan, at least one leg of the pair of legs including a code embedded portion,
wherein the cartridge assembly includes a first sensor for detecting a position of the code embedded portion, wherein the cartridge assembly defines a retention channel for accommodating therein the surgical staple and the first sensor is exposed in the retention channel, wherein the first sensor is in direct contact with the code embedded portion when the surgical staple is properly loaded in the retention channel prior to the formation of the surgical staple, the anvil assembly including a second sensor for detecting the position of the code embedded portion when the surgical staple is in contact with the anvil assembly.

2. A surgical stapling instrument comprising:
a surgical staple including a code embedded portion; and
a tool assembly including a cartridge assembly and an anvil assembly selectively positionable relative to the cartridge assembly about a pivot, the cartridge assembly including a first sensor for detecting a position of the code embedded portion of the surgical staple, the anvil assembly including a second sensor for detecting the position of the code embedded portion of the surgical staple when the surgical staple is in contact with the anvil assembly,
wherein the first sensor is configured to detect a position of the code embedded portion of the surgical staple in an unformed state, and the second sensor is configured to detect the position of the code embedded portion of the surgical staple in a formed state.

3. The surgical stapling instrument according to claim 2, wherein the surgical staple includes a backspan and a pair of legs extending from the backspan, at least one of the pair of legs including the code embedded portion.

4. The surgical stapling instrument according to claim 3, wherein the cartridge assembly defines a retention channel for accommodating therein the surgical staple and the first sensor is disposed adjacent the retention channel.

5. The surgical stapling instrument according to claim 4, wherein the first sensor aligns with the code embedded portion when the surgical staple is properly loaded in the retention channel prior to the formation of the staple.

6. The surgical stapling instrument according to claim 4, wherein the first sensor is exposed in the retention channel.

7. The surgical stapling instrument according to claim 6, wherein the first sensor is in direct contact with the code embedded portion when the surgical staple is properly loaded in the retention channel prior to the formation of the surgical staple.

8. The surgical stapling instrument according to claim 3, wherein the anvil assembly defines a concavity and the second sensor is disposed adjacent the concavity.

9. The surgical stapling instrument according to claim 8, wherein the code embedded portion of the surgical staple aligns with the second sensor after a proper formation of the surgical staple.

10. The surgical stapling instrument according to claim 8, wherein the second sensor is exposed in the concavity.

11. The surgical stapling instrument according to claim 10, wherein the second sensor is in direct contact with the code embedded portion after a proper formation of the surgical staple.

12. The surgical stapling instrument according to claim 8, wherein the concavity includes a pair of recesses, each recess being configured to deform respective leg of the surgical staple.

13. The surgical stapling instrument according to claim 12, wherein the second sensor is disposed adjacent one of the pair of recesses such that the code embedded portion of the surgical staple aligns with the second sensor after a proper formation of the surgical staple.

14. The surgical stapling instrument according to claim 12, wherein the second sensor is exposed in one of the pair of recesses such that code embedded portion of the surgical staple is in a direct contact with the second sensor after a proper formation of the surgical staple.

* * * * *